United States Patent [19]
Carter

[11] Patent Number: 4,870,963
[45] Date of Patent: Oct. 3, 1989

[54] RESPIRATORY AID DEVICE

[75] Inventor: William Carter, Indianapolis, Ind.

[73] Assignee: Carol Bussell, Fort Myers, Fla.

[21] Appl. No.: 190,960

[22] Filed: May 6, 1988

[51] Int. Cl.$^4$ .............................. A62B 9/02; A62B 7/02
[52] U.S. Cl. ............................ 128/205.24; 128/205.25; 128/207.12
[58] Field of Search ................. 128/204.18, 204.24, 128/205.11, 205.18, 205.25, 205.24, 206.28, 207.12, 207.16, 206.15, 206.21, 206.12

[56] References Cited

U.S. PATENT DOCUMENTS

| | | | |
|---|---|---|---|
| 433,418 | 7/1890 | Nütz | 128/205.24 |
| 1,162,416 | 11/1915 | Jeter | 128/207.12 |
| 3,721,238 | 3/1973 | Wise et al. | 128/205.24 |
| 4,323,064 | 4/1982 | Hoenig et al. | 128/205.24 |
| 4,428,392 | 1/1984 | Jones et al. | 128/205.24 |
| 4,454,893 | 6/1984 | Orchard | 128/205.24 |
| 4,509,551 | 4/1985 | Luper | 128/204.23 |

Primary Examiner—Edgar S. Burr
Assistant Examiner—Kimberly L. Asher
Attorney, Agent, or Firm—Robert A. Spray

[57] ABSTRACT

A continuously positive-pressure respiratory aid, providing positive-pressure inhalation and exhalation of a patient suffering from apnea or other respiratory disorder in which forced breathing-assistance is to be administered. A source of pressurized air, an outlet to a face mask, and a vent outlet all are in parallel communication; and the vent is controlled by a spring-pressed valve body which is adjustable to control the above-atmospheric pressure to individual patient's needs. A safety feature provides that the valve body is sufficiently in vent position for the patient's exhalation even if the valve body is somehow blocked from its normal vent movement; and a viscous grease in the support of the valve body prevents objectionable resonant chatter.

14 Claims, 1 Drawing Sheet

U.S. Patent    Oct. 3, 1989    4,870,963
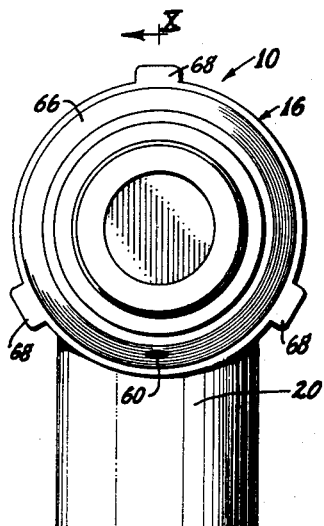
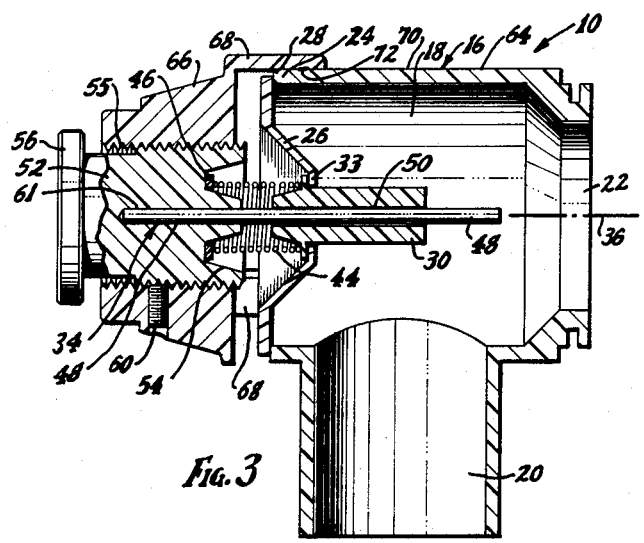
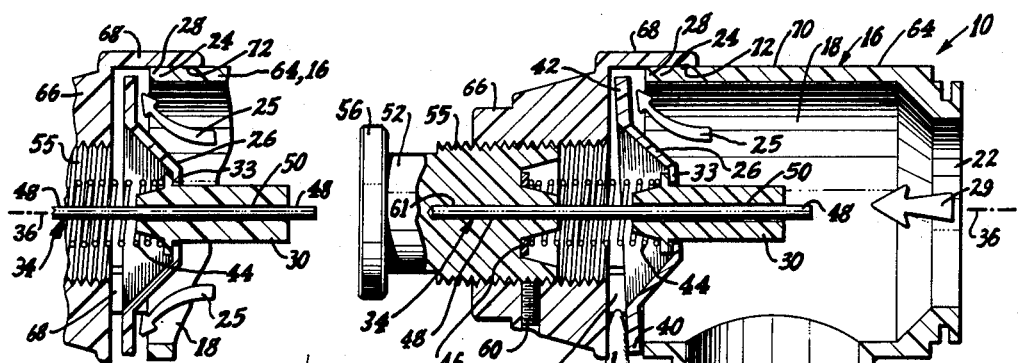
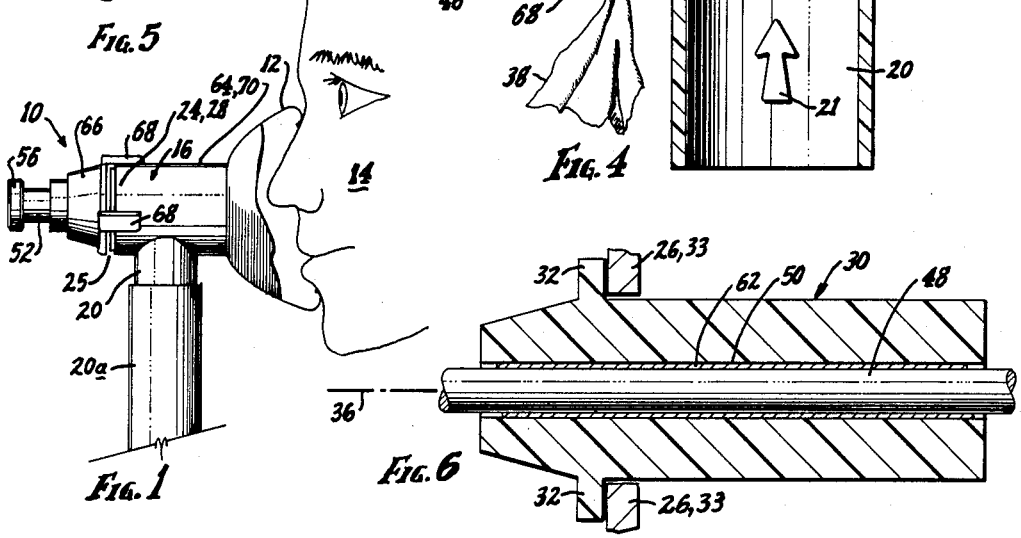
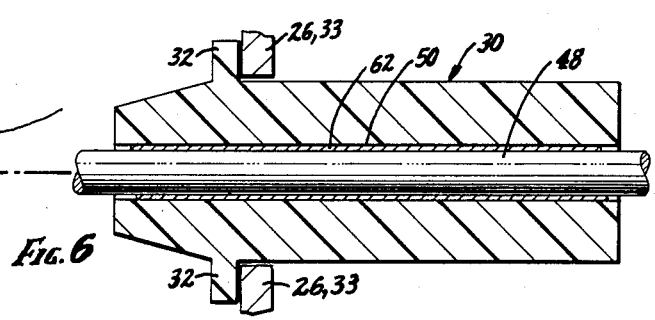

RESPIRATORY AID DEVICE

FIELD OF THE INVENTION, AND INTRODUCTION

The present invention relates to a respiratory aid device, and more particularly to such devices in systems particularly useful to provide assisted breathing for those persons who need a forced-breathing therapy, and more particularly as primarily now considered the provision of continuously positive pressure of air to force inhalation and permit exhalation of air, having reference to a person having respiratory problems such that air under pressure is forced upon the patient in alleviating his distress and breathing difficulties.

Even more particularly, as presently considered, equipment of the type of this invention is expecially considered for use in the treatment and distress-relieving of a disease known as apnea, which is a respiratory disorder in which patients fail to breathe sufficiently or properly during sleep, recognized types being obstructive sleep apnea and central sleep apnea.

These are dreadful conditions, sometimes even life-threatening, and at least can cause devastating changes of personality, family life problems, diminished work performance, irritability, impotence, insomnia, memory loss, etc., as the patient undergoes the loss of breathing repeatedly during sleep. A minimum of such episodes is considered medically significant, for example if there are more than five episodes of cessation of airflow for at least ten seconds each, per hour of sleep.

Any other respiratory problem complicates the condition.

Tracheotomy, tonsillectomy, and uvulopalatopharyngoplasty, and combinations thereof, have been used to try to surgically correct the condition or alleviate the symptoms; and various drug therapies, and physical equipment such as rocking beds, iron lungs, body shells, and various ventilators have been tried.

Forms of ventilators known as CPAP (continuous positive airway pressure) have helped reduce the number of tracheotomies, these being devices with a blower/motor assembly, a flexible hose, and a tight-fitting nasal mask, by which air (sometimes with extra oxygen, and/or humidity control) is forced onto a patient, the pressure being always above atmospheric (i.e., "continuously positive"), thus above atmospheric during inhalation as well as exhalation.

And even though the use of CPAP ventilators is a significant bother and nuisance to a patient, it is better than many alternatives, so a patient has no realistic alternative to their use.

The above is given as an introduction to the long-recognized problems in this field, and the attempts to cure or relieve these problems, generally from the article "Broken Sleep," by Terrie Weaver and Richard P. Millman, as published in *American Journal of Nursing* (February, 1986) p. 146–150, having an extensive bibliography.

The therapy of giving a patient forced breathing poses special needs; for, even at best, a patient finds that breathing through a mask-type facial unit is quite unnatural, and thus quite non-conducive to sleep and comfort. Even minimal noises of the room, or of the blower unit, etc., add to the unpleasantness and sleep difficulty.

A patient can be almost overcome with fright, if there is any disruption at all of breathing, even for a second or so, and even if the patient could instantly pull off the face mask in case of any malfunction.

An inherent source of problem is that the pressure of inhalation has to be high enough to cause air to enter the lungs yet low enough to not cause the patient too much bother to exhale against that pressure, all this requiring some criticality of adjustment of the pressure control; and to make the problem more difficult, the exhalation requires some vent or openness of an outlet for exhalation venting, yet that very openness inherently permits some debris or other foreign agent to somehow get into the working parts and block the operativity of the valve-closure body, and thus block all or most all exhalation needed to permit the interchange of a new supply of air by riddance of air whose oxygen has been used.

Thus, the problems of the need to assure both inhalation and exhalation, with an over-atmospheric pressure being constantly confronting the patient's nose and mouth, are the problems of a CPAP system; and the combination device of the present invention particularly also includes means to assure exhalation in spite of the type of blockage mentioned above.

PRIOR ART RESPIRATORY AID DEVICES DO NOT PROVIDE THE PARTICULAR ADVANTAGES AND CHARACTERISTICS HERE ACHIEVED

In considering the nature of the respiratory aid device and its operativity and safety concepts, and contrasting the inventive nature of the present concepts over prior art devices as known to the inventor, it is not only conceded but emphasized that there are prior art pneumatic devices which can provide air to a patient and permit exhalation, etc., as are factors of background as to the present device and its operativity.

However, of such devices of the prior art as known to the inventor, none have the particular advantages of the present invention. That is, none are known which provide fool-proof safety, with infinitely small increments of pressure-adjustment, etc., and provide relative comfort and ease to the patient, whose forced breathing-assistance is inherently bothersome at best, the features of the device thus giving special and particular advantages of the combination provided by the present invention.

Thus, although it is even emphasized that prior art devices have certain features upon which it could be said that this invention builds, such as inlets, outlets, valve members, springs for biasing valve members, relatively movable associated parts which permit one nature of movement to one part even though the associated part is supported such that it cannot move in that manner, valve cages, screw-type connectors, etc., none known to the inventor provide or achieve the particular and advantageous construction, operativity, and safety features of the present invention, all in spite of a long-recognized great need for human comfort and human safety, etc., all showing that conceptually here the differences from the prior art are of inventive nature, as will become more apparent as the detailed features are pointed out and considered more specifically as to nature and effect.

THE PRESENT INVENTION, SUMMARIZED

It is against the background of such prior art of many years, which fails to provide the advantages of comfort, and adjustability or the advantageous use and safety concepts here shown to be achieved, that the concepts and combination-nature of the present device are rightly and realistically to be considered.

Especially providing advantage in respiratory therapy for severe conditions of apnea, but useful for any situation or condition in which continuously positive air pressure (for both inhalation and exhalation) is useful providing the advantages of both comfort and effect as herein mentioned, the inventive concepts may be considered as summarized as a respiratory aid device having the novel combination of both pressurized breathing-assistance, maximal adjustability as to pressure, safety against an inadvertent blockage of exhalation, etc., by novel features of the combination, including screw-adjustable venting-pressure control, relatively movable members achieving the safety of permitting exhalation even in spite of blockage of the valve disk, with other features of the mechanical-pneumatic system in the combination, thus achieving comfort, sleep-breathing assistance, ease of adjustment to the needs of each patient, and requiring minimal servicing or other maintenance, all with the safety advantage of avoiding the hardship of a blockage of exhalation by a closure valve disk, etc. Other features add to the overall desirability.

By the features thus summarized, and particularly by them in their effect as a combination, and in contrast to the prior art known to the inventor and to what even by hindsight might be asserted as suggestions from the prior art, in the overall consideration the present invention provides an advantageous and novel respiratory aid device and installation.

Accordingly, although various separate concepts and components of respiratory aid devices, with pneumatic and mechanical principles, have been known by which the invention could have been achieved if the concepts of combination had been conceived, for many years, and with great need of this device for human comfort and therapy, nevertheless, the prior art not having had the particular concepts and details as here presented and as shown as different from the prior art as to the expecially-significant factor of the overall combination, even only a fair amount of realistic humility, to avoid consideration of this invention improperly by hindsight, requires the concepts and the advantageous achievement to be realistically viewed as inventive in their nature.

BRIEF DESCRIPTION OF THE DRAWINGS

The above description of the novel and advantageous respiratory aid device of the present invention is of somewhat introductory and generalized form. More particular details, concepts, and features are set forth in the following and more detailed description of an illustrative embodiment, taken in conjunction with the accompanying drawings, which are of somewhat schematic and diagrammatic nature, for showing the inventive concepts of the present invention as are illustrated in this embodiment.

FIG. 1 is an elevation view of a respiratory aid device according to a preferred embodiment, showing a patient provided with a face mask illustrating the use of the device, the mask being shown pictorially in a sectional view to illustrate its use as described herein, a positive pressure procedure for forced breathing, providing an over-atmospheric pressure both during inhalation, exhalation, and whatever may be the dwell periods inbetween;

FIGS. 2-5, in large scale, are views of the respiratory aid device itself, FIGS. 3-5 being generally in axial cross-section as indicated by Section-line X—X of FIG. 2, and with FIG. 5 being of fragmental detail nature;

FIG. 2 is an elevation view looking at the front of the device, i.e., the end opposite that to which the patient's face mask is fitted;

FIG. 3 shows the parts in a valve-closed position, in which the movable pressure-adjustment body here is shown as having been moved to a relatively high pressure-control of the patient's breathing, the set screw then having been tightened to hold that pressure-control adjustment; and the device in this view is shown to illustrate the valve body being shown in valve-closing or non-venting position as urged by the spring which adjustably controls the forced breathing pressure;

FIG. 4 is a similar view, but showing the adjustment body adjusted to a relatively low-pressure setting of the control spring which controls the forced breathing of the patient, this view as in FIG. 5(but in contrast to FIG. 3) showing the closure valve body in open or vent position; however, this FIG. 4 also illustrates how the device avoids malfunction when a piece of debris has accidentally been wedged into a problem-causing position blocking a portion of the closure valve body from moving to the open or venting position, this malfunction-avoidance being by the relative movement of the device's control body means and the closure valve body, even though non-axial movement of the control body means is prevented by its support pin;

FIG. 5 is a fragmental or detail view of the device, the closure valve body being shown in open or venting position, against the bias of the control spring at that position of adjustment of the movable adjustment body which is screwthreadedly connected to the overall body member of the device shown in FIGS. 1-4; and as in FIG. 4, the adjustment body is in a relatively low-pressure setting of the control spring;

FIG. 6 is an axial cross-sectional view, in larger scale, of the control body means shown in FIGS. 3-5, mounted on its support pin, and fragmentally showing its engageability with the closure valve body shown in those Figures.

DETAILED DESCRIPTION OF ILLUSTRATIVE EMBODIMENT OF THE INVENTION

As shown in the drawings, the inventive concepts provide a new and advantageous respiratory aid device 10 for providing positive pressure inhalation and exhalation for a patient.

The device 10 carries a face mask body 12 which fits over the nose and mouth of a patient 14; and the device 10 and mask body 12 provide forced breathing assistance for minimizing the problems of apnea and other respiratory disorders, and as described herein, the device 10 provides adjustability to conform the operativity to the particular needs of individual patients.

The external shell or housing for the device 10 is a body member means 16; and the body member means 16 provides interiorly a chamber 18 with operativity detailed herein.

The body member means 16 has three pneumatic features. That is, the body member 16 has an inlet means 20 which is in communication with an associated source (20a) of pressurized respiratory air (arrow 21) for the patient, and two outlets from the chamber 18, those being a first outlet means 22 communicating with the patient's face mask body 12 and a second outlet means 24 which provides a vent (arrows 25) of the patient's exhalation, and of inlet air 21 which is not being used by the patient's inhalation.

All of those pneumatic features, i.e., the inlet means 20, the first outlet means 22, and the second outlet means 24 are in communication with the chamber 18 of the body member means 16; and by adjustable features explained herein, the device 10 provides that the vent outlet 24 is controlled, so that minimum effort is required by the patient during exhalation even though the patient is always confronted by air at over-atmospheric pressure.

The venting or second outlet means 24 is provide with a closure valve body 26, and there is a valve seat means 28 associated with that second outlet means 24, the valve body 26 and the valve seat 28 regulating the venting 25.

With reference to its operativity, the closure valve body 26 is movable into and between two positions, i.e., (a) toward or into a closed position (FIG. 3) of non-venting, in which the closure valve body 26 operatively seats against the valve seat means 28, for assuring the pressure in the inlet means 20 to impart pressure for forced inhalation by the patient by pressurizing the first outlet means 22 and the face mask body 12, instead of being vented (25) out the second outlet means 24, and (b) (FIG. 5) an open position of venting (arrow 25) the body member means chamber 18 of both the pressure in the inlet means 20 and the pressure in the first outlet means 22 and face mask body 12; and whether or not the control (described below) of the valve body 26 is such that it is open to vent excess air during periods of dwell and inhalation it would be set to be open during periods of exhalation (arrow 29) by the patient.

Interiorly of the body means 16 there is provided a control body means 30, which is relatively movable with respect to the closure valve body 26; and the control body means 30 has abutment means 32, here shown as side-lugs, which abuttingly engage the closure valve body 26, that engagement being shown as against the central portions 33 of the closure valve body 26.

Shown generally by reference numeral 34 there are provided support means 34 for the control body means 30, which support means 34 support the control body means 30 so as to provide it to be movable in its control of the closure valve body 26; and its movement is along an axis 36 which is perpendicular to the general plane of the valve seat means 28 against which the closure valve body 26 seats or tends to seat in its relatively closed position (FIG. 3) of non-venting.

The control body means 30, more particularly, is movable along that axis 36 in and between (a) a first position (FIGS. 3 and 6) in which its abutment lugs 32 abuttingly engage the closure valve body 26(33) to push the closure valve body 26 in an upstream (rightward) direction to its said closed position (FIG. 3) of non-venting, or hold it in such closed position, and (b) a second positon (FIG. 5) in which, even though its abutment means or lugs 32 may be abuttingly engaging the closure valve body 26(33), its abutment means 32 is not pushing the closure valve body 26 sufficiently to cause it to be in its closed (FIG. 3) non-venting position.

Further as to operativity, the relative movability of those two members, i.e., the control body means 30 and the closure valve body 26, provides the great safety feature that if debris 38(FIG. 4) or other cause does cause a portion 40 of the closure valve body 26 to be in its closed position of non-venting, the closure valve body 26 is rockable, i.e., pivotally movable (FIG. 4) with respect to the control body means 30 such as to provide that other portions 42 of the closure valve body 26 are permitted to be in an open position, venting (arrow 25) the chamber 18 of the body member means 16,thus accommodating the patient's exhalation (29), as illustrated in FIG. 4. (The cloth 38 represents any external cause which would block a portion 40 of disk 26 from moving to vent position.)

There is a spring means 44, here shown as a compression spring 44, which as shown is operatively bottomed against the body member means 16, here shown as seating against an anti-friction disk or ring 46, and the control body means 30, here shown as seating against its abutments 32; and the spring 44 biases the control body means 30 toward or into its first position (FIG. 3) of closed and non-venting position of the closure valve body 26, the spring 44 being adjustably set (as explained below) to hold the valve body 26 in such closed position such that minimum effort is required of the patient to exhale against the above-atmospheric pressure in the chamber 18, yet above atmospheric so as to provide forced inhalation.

More particularly as to the support means 34 for the control body means 30, that support 34 as shown is provided by a support pin means 48 which supportingly engages both the body member means 16 and the control body means 30; and the support pin 48 provides relative movement between the body member means 16 and the control body means 30 so that the safety function described as shown in FIG. 4 can be achieved, i.e., the valve-closure effect of the closure valve body is not fully a result of a valve-closing debris 38 somewhere around the periphery of the valve body 26.

It is to be further noted that the relative movement and the support 34 provided by the pin means 48 includes the provision that the control body means 30 is provided by an opening means 50, axially extending parallel to the axis 36, which slidably receives the pin means 48, and the pin means 48 is held fixed to the body member means 16 as mentioned below as to the embodiment shown in the drawings.

Turning now to the pressure-adjustability, for achieving pressure-control as to individual needs, the body member means 16 is provided with an adjustment body 52, shown here as a large cylinder. The adjustment body 52 is the part of the body member means 16 against which the spring means 44 operatively bottoms; and the upstream end of the adjustment body 52 is shown as having an annular recess 54 which receives the disk 46 and the downstream end of the spring 44.

Further as to its operativity, the adjustment body 52 is provided with a movable connection 55 to the body member means 16; and that adjustment of the relative position of the adjustment body 52 with respect to the body member means 16 is what achieves an adjustment of the bias of the spring means 44. That adjustment is facilitated by the adjustment body 52 having a knob 56 on its end (leftward as shown) opposite the end having the annular groove 54.

The movable connection (55) of the adjustment body 52 and the body member means 16 is a screw thread connection 55; and this provides not only a supportive although movable connection 55 of the adjustment body 52 with respect to the body member means 16 but also provides operatively infinitely small increments of adjustability of the bias of the spring means 44, as is desired to fit the apparatus and its therapy to the needs of the individual patient.

A set screw 60 is shown carried by one of the adjustment body 52 and the body member means 16 for fixing the setting of the movable connection 55 of the adjustment body 52 and the body member means 16, thus fixing the bias of the spring means 44. This also fixes the support pin 48 to the body member means 16, for in the form shown the pin 48 is held in a hole 61 in the adjustable body 52.

Resonant chatter of the closure valve body 26 is minimized by a coating of viscous substance, preferably a non-hydrocarbon greasy lubricant 62, between the support pin 48 and the opening 50 in the control body means 30; and the viscosity provides what is believed to be describable as a fluid friction shear effect which retards or dampens undue vacillating movement of the valve disk 26 which would create any sleep-disturbing noise.

Assembly of the interior components is shown by the provision that the body member means 16 comprises at least two portions 64 and 66, one (64) of which portions provides the main chamber 18, and the adjustment body 52 is carried by the other body-portion 66; and in the form shown the two portions 64 and 66 of the body member means 16 are interconnected by leg means 68 extending from one of the two portions (64/66) of the body member means 16 and embracingly retained on the other of those portions (64/66).

That retention in the form shown is shown by three leg-bodies 68 extending generally parallel to the axis 36, from locations generally equally spaced around the periphery of the body-portion 66; and the legs 68 are shown attached to the outer wall 70 of the body-portion 64 by cement 72, the legs 68 and the body-portion 64 thus also serving as a valve cage for the closure valve body 26.

CONCLUSION

It is thus seen that a respiratory aid device, constructed and operatively arranged according to the inventive concepts herein set forth, provides novel concepts of a desirable and usefully advantageous device, yielding advantages which are and provide special and particular advantages when used in a continuously positive-pressure respiratory system, providing positive pressure inhalation and exhalation of patients having a severe condition of apnea or other respiratory disorder.

In summary as to the nature of the overall device's advantageous concepts, their novelty and inventive nature is shown by novel features of concept and construction shown here in advantageous combination and by the novel concepts hereof not only being different from all the prior art known, even though respiratory aid devices have been known and although pneumatic and mechanical principles are known by which this invention could have been achieved, but because the achievement is nevertheless not what is or has been suggested to those of ordinary skill in the art, especially realistically considering this as a combination comprising components which individually are similar in nature to what is well known to most all persons of technical or medical equipment skill, surely including most of the many makers, technicians, and service personnal as to medical equipment for many years. No prior art component or element has even suggested the modifications of any other prior art to achieve the particulars of the novel concepts or the overall combination here achieved, with the special advantages which the overall device provides; and this lack of suggestion by any prior art has been in spite of the worldwide and increasing use of medical equipment and pneumatic-mechanical devices of various kinds.

The differences of concept and construction are specified herein, yielding advantages needed for years to relieve and treat human suffering, during all of which this present invention has not been suggested to or by the very commercial and highly competitive medical equipment field, nor users for which this invention would have been greatly advantageous. All of that lack of this invention by all those persons has been in spite of the relative simplicity of the construction once the concepts have been conceived, in spite of the lessening of human suffering and in spite of the advantages this invention would have given, and in spite of the availability of all the materials, and much known-how as to pneumatic-mechanical devices, to untold number of persons the entire world over.

Any particularly is the overall difference from the prior art significant when the non-obviousness is viewed by a consideration of the subject matter of this overall device as a whole, as a combination integrally incorporating features different in their combination from the prior art, in contrast to merely separate details themselves, and further in view of the prior art respiratory aid concepts and devices not achieving particular advantages here achieved by this combination.

Accordingly, it will thus be seen from the foregoing description of the invention according to this illustrative embodiment, considered with the accompanying drawings, that the present invention provides new and useful concepts of a novel and advantageous respiratory aid device having and yielding desired advantages and characteristics in formation and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment, or form or arrangement of parts herein described or shown.

I claim:

1. A respiratory aid device carrying a face mask body which fits over the nose and mouth of a patient, the device and mask body providing positive pressure inhalation and exhalation for a patient, comprising, in combination:

a body member means having a chamber;

the body member means having an inlet means for communicating with an associated source of pressurized respiratory air for the patient, a first outlet means communicating with the patient's face mask body, and a second outlet means which provides a vent;

the inlet means, the first outlet means, and the second outlet means being in communication with the chamber of the said body member means;

the second outlet means being provided with a closure valve body having inner and outer perimeters, a valve seat means associted with the second outlet means;

a control body means carrying said closure valve body and being relatively movable with respect to the closure valve body, and having abutment means which abuttingly engage the closure valve body adjacent its inner perimeter and said seat means being engagable with said closure valve body around its outer perimeter;

said closure valve body being movable into and between positions of (a) toward or into a closed position of non-venting, where the inlet means imparts pressure to the first outlet means and face mask body and hence to the patient for inhalation instead of being vented out the second outlet means, and (b) an open position of venting the body member means chamber of both the pressure in the inlet means and the pressure in the first outlet means and face mask body, during periods of exhalation by the patient, and to vent excess air not being used during periods of dwell and inhalation;

means permitting said closure valve body to move into a partially open position even when a portion of said closure valve body is accidently restrained against movement from said closed position, said means including a rockable mounting for said closure valve body on said control body means;

there being provided support means for the control body means which support the control body means so as to enable it to move along an axis perpendicular to the general plane of the valve seat means, said control body being movable along said axis between three different positions, including; (a) a first position in which the entirety of the abutment means and the entirety of the valve seat means both engage said inner and outer perimeters of said closure valve body, respectively, (b) a second position in which said inner perimeter of said closure valve body engages the entirety of said abutment means and the outer perimeter of said closure valve boyd is spaced from said valve seat, and (c) a third position constituting said partially open position in which the inner and outer perimeters of said closure valve body engage only a portion of said abutment means and said valve seat means, respectively;

the relative movability of the control body means and the closure valve body providing that if debris or other external cause prevents a portion of the closure valve body from being moved from said closed position of non-venting, the closure valve body is movable with respect to the control body means, thereby providing that other portions of the closure valve body are permitted to be moved to the open position to vent the chamber of the body member means.

2. The invention according to claim 1, in a combination in which there is a spring means operatively bottomed against the body member means and the control body means, biasing the control body means toward its said closed and non-venting position of the closure valve body.

3. The invention according to claim 2, in a combination in which the spring means is a compression spring.

4. The invention according to claim 2, in a combination in which the support means for the control body means is provided by a pin means which supportingly engages both the body member means and the control body means, and provides relative movement between the body member means and the control body means.

5. The invention according to claim 4, in which the relative movement and the support provided by the pin means includes the provision that the control body means is provided by an opening means which slidably receives the pin means, and the pin means is held fixed to the body member means.

6. The invention according to claim 5, in a combination in which the body member means is provided with an adjustment body, the adjustment body being the part of the body member means against which the spring means operatively bottoms.

7. The invention according to claim 6, in a combination in which the adjustment body and the body member means are provided with a movable connection providing that adjustment of the relative position of the adjustment body with respect to the body member means achieves an adjustment of the bias of the spring means.

8. The invention according to claim 7, in a combination in which the movable connection of the adjustment body and the body member means is a screw thread connection, providing not only a supportive although movable connection of the adjustment body with respect to the body member means but also provides operatively infinitely small increments of adjustability of the bias of the spring means.

9. The invention according to claim 8, in a combination in which there is a set screw carried by one of the adjustment body and the body member means for fixing the setting of the movable connection of the adjustment body and the body member means, thus fixing the bias of the spring means.

10. The invention according to claim 5, in a combination in which there is provided a viscous substance between the pin means and the opening means of the control body means, minimizing resonant chatter movement of the closure valve body.

11. The invention according to claim 6, in a combination in which the body member means comprises at least two portions, one of which portions provides the said chamber, and the said adjustment body is carried by the other portion.

12. The invention according to claim 11, in a combination in which the two portions of the body member means are interconnected by leg means extending from one of the two portions of the body body member means and embracingly retained on the other of the said portions.

13. The invention as set forth in claim 4, in a combination in which the body member means is provided with an adjustment body which both supports the pin means and is connected to the body member means by a screw thread connection, providing not only a supportive although movable connection of the adjustment body with respect to the body member means but also provides operatively infinitely small increments of adjustability of the bias of the spring means.

14. The invention according to claim 13, in a combination in which there is provided a viscous substance between the pin means and the opening means of the control body means, minimizing resonant chatter movement of the closure valve body.

* * * * *